United States Patent [19]

Kanner et al.

[11] Patent Number: 4,599,441

[45] Date of Patent: Jul. 8, 1986

[54] PROCESS FOR PREPARING ORGANOHALOSILANES UTILIZING COPPER HALIDE-ALUMINUM HALIDE CATALYSTS

[75] Inventors: Bernard Kanner, West Nyack; Kenrick M. Lewis, Rego Park, both of N.Y.

[73] Assignee: Union Carbide Corporation, Danbury, Conn.

[21] Appl. No.: 781,458

[22] Filed: Sep. 30, 1985

[51] Int. Cl.$^4$ .............................. C07F 7/08; C07F 7/12
[52] U.S. Cl. .................................................... 556/469
[58] Field of Search ......................................... 556/469

[56] References Cited

U.S. PATENT DOCUMENTS

| | | | |
|---|---|---|---|
| 2,380,995 | 8/1945 | Rochow | 260/607 |
| 2,647,136 | 7/1953 | Sauer | 260/448.2 |
| 2,717,257 | 9/1955 | Bluestein | 260/448.2 |
| 2,746,981 | 5/1956 | Wagner et al. | 556/469 |
| 2,786,861 | 3/1957 | McEntee | 260/448.2 |
| 2,888,478 | 5/1959 | Ashby | 556/469 |
| 3,346,399 | 10/1967 | Harding et al. | 556/469 |
| 3,420,908 | 1/1969 | Sherk et al. | 260/667 |
| 3,592,865 | 7/1971 | Long et al. | 260/667 A |
| 3,637,780 | 1/1972 | Bazouin et al. | 556/469 |
| 3,647,843 | 3/1972 | Walker et al. | 260/438.1 |
| 3,651,159 | 3/1972 | Long et al. | 260/667 |
| 3,655,710 | 4/1972 | Bazouin et al. | 556/469 |
| 3,793,357 | 2/1974 | McEntee | 260/448.2 |
| 3,846,503 | 11/1974 | Schmerling et al. | 260/666 |
| 3,846,504 | 11/1974 | Schmerling et al. | 260/666 |
| 3,935,288 | 1/1976 | Riegel | 260/656 |

OTHER PUBLICATIONS

Zemany et al., Kinetics and Thermodynamic Properties of the Disproportionation of Methylchlorosilanes, J. Amer. Chem. Soc., 70, p. 4222 (1948).

Golosova et al., "Equilibria in the Disproportionation Reactions of Alkylchlorosilanes," Russ. J. Phys. Chem. 45, p. 460 (1971), (Eng. Translation).

Morosov et al., "Formation of Chlorotrimethylsilane as a Result of Secondary Disproportionation Processes of Dichlorodimethylsilane," Russ. J. Gen. Chem., 39, p. 2234 (1969) (English Translation).

Schlapfer et al., "Resonance Raman Spectra and Structure of the Vapor Complexes Formed by $CuCl_2(g)$ and $LCl_3(g)(L=Al, Ga, In)$", Inorganic Chemistry, 17 (6), p. 1623 (1978).

*Primary Examiner*—Paul F. Shaver
*Attorney, Agent, or Firm*—P. W. Leuzzi

[57] ABSTRACT

This invention relates a process for the redistribution/-disproportionation of organohalosilanes utilizing copper halide-aluminum halide complex catalysts.

26 Claims, No Drawings

PROCESS FOR PREPARING ORGANOHALOSILANES UTILIZING COPPER HALIDE-ALUMINUM HALIDE CATALYSTS

FIELD OF THE INVENTION

This invention relates to a novel process for the preparation of organohalosilanes utilizing copper halide-aluminum halide catalysts. In particular, this invention relates to a process for the redistribution, e.g., disproportionation, of organohalosilanes utilizing copper halide-aluminum halide complex catalysts. More particularly, this invention relates to a process for the preparation of triorganohalosilanes by the redistribution of diorganodihalosilanes in the presence of copper halide-aluminum halide complex catalysts.

BACKGROUND OF THE INVENTION

Organohalosilanes have found many uses in the chemical arts. By way of illustration, certain organohalosilanes, such as trimethylchlorosilane, are useful as silylating agents, polymer end-blockers and capping reagents in organic and pharmaceutical synthesis. Several processes for the preparation of organohalosilanes have been proposed. For example, methylchlorosilanes can be produced by the "direct reaction" of methyl chloride with a silicon-copper mass (see, e.g. U.S. Pat. No. 2,380,995).

The direct reaction produces a mixture of organochlorosilanes (e.g. dimethyldichlorosilane and trimethylchlorosilane). Usually more dimethyldichlorosilane and less trimethylchlorosilane are produced by the direct reaction than are required commercially.

Redistribution (e.g., disproportionation) methods are also known in the art for the preparation of organohalosilanes, particularly for converting excess dimethyldichlorosilane to needed trimethylchlorosilane. Some of these methods utilize aluminum catalysts and reactants, such as AlCl$_3$, and other aluminum-containing materials. A silane redistribution reaction is a rearrangement of at least two different substituents which are attached to a silicon atom or atoms. One or more silanes having at least two substituents, such as CH$_3$ or Cl, redistribute when these substituents exchange sites of bonding to silicon. The resulting silane or silanes still have a total of four substituents or atoms attached to the silicon atom, but in ratios different from that of the starting silane or silanes. A typical silane redistribution reaction can be illustrated by the following equation:

$$(CH_3)_4Si + (CH_3)_2SiCl_2 \rightleftharpoons 2(CH_3)_3SiCl$$

A silane disproportionation reaction is a type of silane redistribution reaction that occurs when a single silane yields two or more dissimilar silanes having substituents (i.e., CH$_3$ Cl) in differing proportions from that of the initial starting silane. A silane disproportionation reaction can be illustrated by the following equation:

$$2(CH_3)_2SiCl_2 \rightleftharpoons CH_3SiCl_3 + (CH_3)_3SiCl$$

This position of thermodynamic equilibrium in the disproportionation of diorganodihalosilanes typically favors a high concentration of the diorganodihalosilane. For example, with dimethyldichlorosilane, the following equilibrium concentrations are observed at 350° C. with 2 weight percent AlCl$_3$:

$$2(CH_3)_2SiCl_2 \rightleftharpoons (CH_3)_3SiCl + CH_3SiCl_3$$
$$71.8 \text{ wt \%} \quad 8.6 \text{ wt \%} \quad 12.6 \text{ wt. \%}$$

(see Zemany et al, J. Amer. Chem. Soc., vol. 70, p. 4222 (1948); Golosova et al, Russ. J. Phys. Chem., vol 45, p. 460 (1971) Engl. Trans.). Disproportionation of diorganodihalosilanes without any catalyst or with the catalysts described by the prior art does not provide a practical commercial synthesis of triorganohalosilanes because equilibrium is attained too slowly or not at all. Consequently, a practical synthesis of triorganohalosilanes by the disproportionation of diorganodihalosilanes requires the use of a catalyst capable of accelerating the attainment of equilibrium. The use of SiH compounds and arylsilanes as co-catalysts with AlCl$_3$ for this purpose is known (See U.S. Pat. Nos. 2,786,861 and 3,793,357).

U.S. Pat. No. 2,717,257 describes the use of alkali metal halogen-aluminates of the general formula, MAlX$_4$, wherein M is an alkali metal and X is a halogen, as catalysts for the redistribution of organohalosilanes.

Morozov et al (Russ. J. Gen. Chem. vol. 41, p. 1275 (1971); vol. 39, p. 2234 (1969) Engl. Trans.) report that the disproportionation of dichlorodimethylsilane is facilitated by the addition of NaAlCl$_4$ to a fixed bed of silicon-copper contact mass in the presence of active methyl chloride molecules on the catalyst surface.

U.S. Pat. No. 2,647,136 states that aluminum chloride was the only catalyst found to accelerate the redistribution of methylchlorosilanes and that the other common Lewis acid catalysts, such as BCl$_3$, ZnCl$_2$, FeCl$_3$ and CuCl, had no perceptible effect on the course of the redistribution reaction.

The use of organoaluminum compounds as catalysts in methylchlorosilane redistribution and disproportionation reactions, in general, often results in pyrophoric, potentially explosive, and readily hydrolyzable organoaluminum by-products which must be disposed via lixiviation with water or alkali. This can be extremely hazardous because of the attendant hydrolysis of methylchlorosilanes to yield hydrogen chloride. Aluminum trichloride has appreciable solubility in methylchlorosilane mixtures which can produce separation and purification problems. Plugging problems in transport lines and distillation columns are usually concomitant with its use. When aluminum trichloride is utilized in conjunction with certain co-catalysts described in the prior art, there is the possibility of product contamination or loss of catalyst by volatization.

Complexes comprising copper halides and aluminum halides are known (see, e.g., Schlapfer, et al, Inorganic Chem., vol. 17, No. 6, p. 1623 (1978); and U.S. Pat. Nos. 3,651,159; 3,647,843; and 3,592,865). These complexes have been utilized in various processes, e.g. in reactions involving the alkylation or halogenation of hydrocarbons (see U.S. Pat. Nos. 3,846,503; 3,846,504; 3,420,908; and 3,935,288). However, prior to the present invention, complexes of aluminum halide and copper halide were not utilized in reactions involving the redistribution of organohalosilanes.

Accordingly, it is an object of the present invention to provide a novel process for the preparation of organohalosilanes utilizing copper halide-aluminum halide complex catalysts.

In particular, it is an object of the present invention to provide a novel process for the redistribution (e.g., disproportionation) of organohalosilanes utilizing a copper halide-aluminum halide complex catalyst.

More particularly, it is an object of this invention to provide a novel process for the preparation of triorganohalosilanes by the catalytic disproportionation of diorganodihalosilanes utilizing a copper halide-aluminum halide complex catalyst.

A further object of this invention is to provide a process for the redistribution of organohalosilanes which does not produce hazardous by-products, involve soluble catalysts, produce product contamination or lose catalyst through volatization.

DESCRIPTION OF THE INVENTION

This invention relates to a process for effecting the redistribution of at least one organic group bonded to a silicon atom by a silicon to carbon bond and at least one halogen atom bonded to a silicon atom which process comprises:
(1) forming a reaction mixture of
 (a) a first silane or first mixture of silanes containing at least one organic group bonded to a silicon atom by a silicon to carbon bond and at least one halogen atom bonded to a silicon atom; and
 (b) a catalytic amount of $AlX_3$ and $CuX_n$ complex wherein n is 1 or 2 and X is a halogen atom; and
(2) maintaining the reaction mixture at a temperature and pressure at which said group and atom in (1)(a) redistribute to form a second silane or a second mixture of silanes different from the first silane or first mixture of silanes.

For the purposes of this invention the catalytically effective complex of $AlX_3$ and $CuX_n$ (hereinafter also referred to as the "catalyst complex") is any complex of $AlX_3$ and $CuX_n$ which can accelerate the rate at which the redistribution is effected and is meant to encompass complexes formed from mixtures of $AlX_3$ and CuX, mixtures of $AlX_3$ and $CuX_2$, and mixtures of $AlX_3$, CuX and $CuX_2$. Preferably all the $AlX_3$ and $CuX_n$ in the catalyst mixture will be complexed and no free (i.e., uncomplexed) $AlX_3$ will be present. Complete complexing can occur when the molar ratio of $CuX_n$ to $AlX_3$ in the catalyst mixture is from about 0.5:1 to about 3:1. The complex formed when the molar ratio of $CuX_n$ to $AlX_3$ is about 0.5:1 is preferred.

Complete complexing of the $AlX_3$ and $CuX_n$, although desirable, is not necessary for a mixture of $AlX_3$ and $CuX_n$ to produce a catalytically effective complex useful in the process of this invention. The catalyst mixture useful in producing the catalyst complex in the process of this invention can comprise a molar ratio of $CuX_n$ to $AlX_3$ of at least about about 0.05:1, preferably from about 0.25:1 to 0.6:1 and most preferably about 0.5:1. The concentration of the total catalyst complex can be as low as 0.1% by weight, based on the total weight of the silane reactant(s) in the reaction complex. Higher concentrations of the catalyst complex will increase the rate of redistribution and decrease the overall reaction time. The upper limit on the concentration of the catalyst complex is not critical and would be determined largely by commercial and economic considerations. As a practical matter, a concentration of catalyst complex of less than 10%, generally between 5-10%, by weight based on the total weight of the silane reactant(s) in the redistribution reaction mixture, is preferred.

The active catalyst complex can be prepared in situ by adding the ingredients of the catalyst mixture, i.e. $CuX_n$ and $AlX_3$, to the redistribution reaction mixture and exposing the resultant reaction mixture to the appropriate temperature and pressure conditions to effect the desired redistribution. Alternatively the active catalyst complex may be preformed by heating the ingredients of the catalyst mixture together, e.g. in a sealed ampoule, and then transferring the catalyst mixture so formed to the redistribution reaction mixture.

The CuX, $CuX_2$, and $AlX_3$ used in the process of this invention should all be anhydrous materials to avoid side reactions between the water of hydration and the organohalosilanes. Additionally, whether the active catalyst complex useful in the process of this invention is preformed or formed in situ, its subsequent handling should be under anhydrous, inert atmospheric conditions in order to avoid hydrolysis and oxidation. Such anhydrous, inert atmospheric conditions are also necessary if reuse of the active catalyst complex without loss of catalytic activity is desired.

The process of this invention can be conducted in the presence of an organic solvent, if desired, provided that the presence of the solvent does not have a deleterious effect on the redistribution reaction. For example, branched aliphatic hydrocarbons, such as 2,5-dimethyl hexane, can be used as solvents because they do not interfere with the redistribution reaction whereas certain aromatic solvents, such as toluene, are not acceptable solvents because they could inhibit the catalytic activity of the $CuX_n/AlX_3$ catalyst complex.

The manner in which the process of this invention can be practiced will vary depending on the choice of silane or mixture of silanes in the redistribution reaction mixture. For example, as described below, the temperature and pressure requirements can vary significantly from those necessary for the disproportionation of a diorganodihalosilane to those necessary for the redistribution of a mixture of organohalosilanes.

A preferred embodiment of this invention relates to a process for the catalytic disproportionation of a diorganodihalosilane of the formulas $$R_2SiX_2 \quad \text{[Formula (1)]}$$

wherein R is alkyl or aryl and X is halogen, which comprises contacting the diorganodihalosilane with a catalytic amount of a complex of $AlX_3$ and $CuX_n$, wherein n is 1 or 2, and X is as defined above, at a temperature greater than 200° C. and under superatmospheric pressure.

The process of this preferred embodiment of this invention is conducted under superatmospheric pressure, preferably from about 400–750 psi, more preferably from about 450–550 psi, and preferably under autogenous conditions. The reaction temperature of the process of this preferred embodiment of this invention can be varied depending on such factors as the particular diorganodihalosilane employed, the pressure utilized, etc. In general, the reaction temperature must be greater than about 200° C., preferably between about 250° C. to about 350° C. and most preferably between about 250° C. to about 300° C. The reaction time will vary (e.g. from about 1 to about 10 hours), depending on factors such as catalyst concentration, reaction temperature, etc., but, in general, when the reaction temperature is between about 250° C.–300° C. and the catalyst complex concentration in the disproportionation reaction mixture is about 5–10% by weight based on the weight of the diorganodihalosilane utilized, using a catalyst mixture wherein the molar ratio of $CuX_n/AlX_3$ is about 0.5:1, the reaction time will be about 4–8 hours.

When the disproportionation reaction of the process of this preferred embodiment of this invention is completed, the triorganohalosilane produced can be distilled from the crude reaction product. If reuse of the $CuX_n/AlX_3$ catalyst complex is desired, a new supply of diorganodihalosilane need only be added to the residue of the distillation and the resultant reaction mixture subjected to the desired appropriate reaction conditions selected from those outlined above.

As stated above, the process of this invention can also be utilized for the redistribution of mixtures of organohalosilanes. Accordingly, another preferred embodiment of this invention relates to a process for the catalytic redistribution of a mixture of organohalosilanes having the formulas:

$$R_mSiX_{4-m} \quad \text{[Formula (2)]}$$

and $$R_pSiHX_{3-p} \quad \text{[Formula (3)]}$$

wherein R and X are as defined above, m is 1 to 4 inclusive and p is 1 to 3 inclusive, which comprises contacting the mixture of organohalosilanes with a catalytic amount of a complex of $AlX_3$ and $CuX_n$. The reaction conditions described above for the disproportionation of diorganodihalosilanes can be used for this redistribution reaction as well, although this redistribution reaction can be conducted at temperatures as low as room temperature or higher and at atmospheric or superatmospheric pressure.

The halogen represented by X in Formulas (1), (2) and (3) above is preferably the same in the organohalosilane and in the complex of $AlX_3$ and $CuX_n$, i.e., if X is Cl in the organohalosilane, then the complex should comprise $AlCl_3$ and $CuCl_n$. This is desirable to avoid obtaining products of the redistribution with different halogen substituents. Preferably R is $C_1-C_4$ alkyl, most preferably methyl, and X is preferably chlorine.

The following Examples are presented to illustrate the process of this invention.

The terms and abbreviations used in the Examples have the following meanings.

| ABBREVIATION | MEANING |
|---|---|
| GC | Gas chromatography |
| GC/MS | Gas chromatography/mass spectrometry |
| °C. | Degree Celsius |
| °K. | Degree Kelvin |
| T °K. | Temperature in degrees Kelvin |
| cm | centimeter |
| $cm^{-1}$ | reciprocal centimeter |
| wt % | weight percent |
| ml | milliliter |
| gm | gram |
| Kcal | Kilocalorie |
| psig | pounds per square inch |
| min | minute |
| hr | hour |
| Temp. | Temperature |
| TC | $HSiCl_3$ |
| MD | $CH_3SiHCl_2$ |
| M | $(CH_3)_3SiCl$ |
| T | $CH_3SiCl_3$ |
| D | $(CH_3)_2SiCl_2$ |
| Q | $(CH_3)_4Si$ |
| DM | $(CH_3)_2SiHCl$ |

STARTING MATERIALS

The $AlCl_3$, CuCl and $CuCl_2$ used in the following Examples were commercial compounds. Commercial CuCl can contain up to about 3 wt % $CuCl_2$. $(CH_3)_2SiCl_2$ was reagent grade material typically of about 99.7 wt % purity.

EXAMPLE 1

This example shows that the mixture of copper chloride and aluminum chloride reacts to form new complex species different from the starting chlorides.

A. 0.43 gm CuCl (0.0043 mole) and 1.11 gm $AlCl_3$ (0.0083 mole) were mixed together in a thick-walled glass ampoule in a glove-bag filled with dry nitrogen. The ampoule was then evacuated, sealed in a flame and subsequently placed in a fluidized sand bed of 300° C. for 15 minutes. On removal from the bed, the ampoule contained a dark colored liquid, which crystallized to a gray solid.

B. A mixture of 0.75 gm $CuCl_2$ (0.0056 mole) and 1.42 gm $AlCl_3$ (0.011 mole) was prepared in A. above and reacted to give yellow crystals.

Each solid sample, still within the sealed ampoule, was then analyzed by Raman Spectroscopy. The principal bands observed are set forth in Table 1 along with comparative data for solid $AlCl_3$. Solid CuCl has no Raman spectrum. The results show that while the solid reaction product samples and solid $AlCl_3$ sample have Raman bands at 305–307 $cm^{-1}$ and 168–170 $cm^{-1}$, the intensity ratios of the bands are different for the three samples. The relative intensity of the band at 307 cm$^{-1}$ to that at 168 cm$^{-1}$ in the CuCl/AlCl$_3$ sample is 1.54, while the corresponding ratio for solid AlCl$_3$ sample is 3.22. The 348 cm$^{-1}$ band in the spectrum of the CuCl/AlCl$_3$ sample is very intense and has no counterpart in the AlCl$_3$ spectrum. It is apparent that the solid reaction product of CuCl and AlCl$_3$ is different from either of the starting materials and gives rise to the Raman vibrations at 168 cm$^{-1}$, 307 cm$^{-1}$ and 348 cm$^{-1}$. Comparison of the data for the CuCl/AlCl$_3$ sample and the CuCl$_2$/AlCl$_3$ sample in Table 1 shows that different complexes are formed.

TABLE 1

| Raman Bands of AlCl$_3$, CuCl$_2$ plus AlCl$_3$ and CuCl plus AlCl$_3$ (Molar Ratio CuCl$_n$/AlCl$_3$ = 0.5) | | |
|---|---|---|
| Solid AlCl$_3$ | Solid CuCl$_2$ + AlCl$_3$ | Solid CuCl + AlCl$_3$ |
| 115 cm$^{-1}$ (w) | 110 cm$^{-1}$ (sh) | 110 cm$^{-1}$ (sh) |
| 170 (m) | 170 (m) | 168 (m) |
| 196 (w) | 93 (vs) | |
| 255 (w) | 268 (vs) | |
| 306 (vs) | 305 (w) | 307 (s) |
| | 352 (m) | 348 (vs) |
| | 395 (m) | |
| | 485 (w) | |

Note:
Abbreviations in parenthesis refer to the relative intensities of the Raman vibration bands. They have the following meanings:
sh = shoulder,
w = weak,
m = medium,
s = strong,
vs = very strong

EXAMPLE 2

This example illustrates the effect of increasing CuCl levels on the yield of (CH$_3$)$_3$SiCl and CH$_3$SiCl$_3$ from the disproportionation of CH$_2$SiCl$_2$ at 264° C. with 5 wt % AlCl$_3$.

Eight separate experiments were conducted (see Table 2 below). In each experiment, 0.40–0.45 mole (CH$_3$)$_2$SiCl$_2$ was placed in 300 ml stainless steel autoclave along with a mixture of 5 wt % AlCl$_3$ and 0–5 wt % CuCl (percentages based on the weight of (CH$_3$)$_2$SiCl$_2$ used). A mixture of AlCl$_3$ and CuCl was weighed out in a nitrogen-filled glove bag, shaken together and then transferred to the autoclave. The sealed autoclave was rocked to mix the reactants, and heated to 264° C. for 5 hours. The pressure attained was 500-550 psig. After cooling the autoclave, the contents of the autoclave were emptied into a dried, nitrogen-flushed, weighed container for subsequent analysis by GC and GC/MS. The composition of the reaction mixtures for the eight experiments is set forth in Table 2. From the literature [J. Amer. Chem. Soc., vol. 70, 4222 (1948); Russ J. Phys. Chem., vol. 45, No. 4, 460 (1971], it can be calculated that the equilibrium concentration of (CH$_3$)$_3$SiCl at 264° C. is 8.35 wt %. The results in Table 2 below show that the yield of (CH$_3$)$_3$SiCl varied with the molar ratio of CuCl to AlCl$_3$ but that complexes of CuCl and AlCl$_3$ (Examples 2B to 2G) were superior catalysts compared to AlCl$_3$ alone (Example 2A). CuCl alone had no catalytic effect on the disproportionation of (CH$_3$)$_2$SiCl$_2$ (Example 2H).

TABLE 2

The effect of CuCl on the Disproportionation of (CH$_3$)$_2$SiCl$_2$("D") by AlCl$_3$ at 264° C., 520–550 psig to produce methyltrichlorosilane ("T") and trimethylchlorosilane ("M")

| Example | Moles D | AlCl$_3$ Wt % | CuCl Wt % | Molar Ratio CuCl AlCl$_3$ | M Wt % | T Wt % | D Wt % |
|---|---|---|---|---|---|---|---|
| 2A | 0.45 | 5.04 | 0 | 0 | 1.45 | 3.27 | 95.28 |
| 2B | 0.45 | 5.02 | 1.04 | 0.28 | 1.64 | 5.46 | 92.90 |
| 2C | 0.46 | 5.01 | 1.86 | 0.50 | 4.80 | 9.70 | 85.50 |
| 2D | 0.43 | 5.02 | 2.15 | 0.58 | 4.50 | 10.0 | 85.50 |
| 2E | 0.42 | 5.01 | 2.47 | 0.66 | 3.15 | 7.16 | 89.69 |
| 2F | 0.43 | 5.04 | 3.74 | 1.00 | 2.73 | 6.41 | 90.86 |
| 2G | 0.41 | 5.06 | 5.06 | 1.35 | 1.89 | 5.11 | 93.00 |
| 2H | 0.42 | 0 | 4.94 | 0 | 0 | 0 | 100.00 |

EXAMPLE 3

This example illustrates the effect of temperature and CuCl/AlCl$_3$ molar ratio on the yield of (CH$_3$)$_3$SiCl and CH$_3$SiCl$_3$ by the disproportionation (CH$_3$)$_2$SiCl$_2$. The data permit the computation of activation energies for the catalytic disproportionation reactions with AlCl$_3$ alone and a CuCl/AlCl$_3$ complex with a molar ratio of 0.5: 1.

Ten separate experiments (3A to 3J) were conducted and the conditions and results are shown in Table 3 below. The procedure and equipment used were the same as those described in Example 2, except that the molar amount of (CH$_3$)$_2$SiCl$_2$ used was between 0.43–0.55 mole, the CuCl/AlCl$_3$ molar ratios were held to 0–1.00 and the temperature was varied from 264° C.–323° C. The time at the stated temperature was five hours in each case. The experimental data are set forth in Table 3.

The yield of (CH$_3$)$_3$SiCl increased between 264° C. and 323° C. at each of the molar ratios studied. At 323° C., the content of (CH$_3$)$_3$SiCl in the reaction mixture was 8.19 wt % at CuCl/AlCl$_3$ molar ratio of 0.26 and 0.50. This value was 85% of the equilibrium concentration (9.6 wt %) calculable from the literature references in Example 2.

The efficacy of a catalyst in effecting disproportionation reactions can be measured by determining the rate of approach to equilibrium as well as the yield of products relative to the equilibrium values at the temperature of the reactions. All the reactions were run for 5 hours at the stated temperatures, so the quantity of (CH$_3$)$_3$SiCl formed is a direct indication of the rate of approach to equilibrium. Accordingly, a plot of log (M wt %) versus 1/T°K. is an Arrhenius plot [see Benson, The Foundation of Chemical Kinetics, McGraw-Hill Book Co., N.Y. (1960), pp. 66–67] from which the activation energy of the reaction can be calculated. A lower activation energy denotes a faster reaction and hence more efficient catalysis.

An Arrhenius plot for the experiments (3A, 3B, 3C) wherein the CuCl/AlCl$_3$ molar ratios were 0.5–0.6 gave an activation energy of 6.53 kcal per mole. The corresponding plot for the AlCl$_3$-catalyzed reaction at 264° C.(537° K.) and 300° C.(574° K.), examples 3I and 3J, respectively gave an activation energy of 21.1 kcal per mole. The disproportionation reactions catalyzed by complexes of CuCl and AlCl$_3$, therefore, proceed at a much faster rate than the reactions using AlCl$_3$ alone. A rate increase of about 10$^6$ can result from using a CuCl/AlCl$_3$ mixture with a molar ratio of 0.5 instead of using AlCl$_3$ alone.

TABLE 3

The effect of Temperature and CuCl/AlCl$_3$ on (CH$_3$)$_2$SiCl$_2$ Disproportionation

| Example | Temp. °C. | Moles D | AlCl$_3$ Wt % | Molar Ratio CuCl/AlCl$_3$ | M Wt % | T Wt % | D Wt % |
|---|---|---|---|---|---|---|---|
| 3A | 264 | 0.43 | 5.02 | 0.58 | 4.50 | 10.0 | 85.50 |
| 3B | 304 | 0.54 | 5.01 | 0.53 | 6.89 | 14.99 | 78.12 |
| 3C | 322 | 0.45 | 5.05 | 0.50 | 8.19 | 17.99 | 73.82 |
| 3D | 264 | 0.43 | 5.04 | 1.00 | 2.73 | 6.41 | 90.86 |
| 3E | 300 | 0.55 | 5.02 | 1.00 | 6.37 | 14.19 | 79.45 |
| 3F | 264 | 0.45 | 5.02 | 0.28 | 1.64 | 5.46 | 92.90 |
| 3G | 323 | 0.44 | 5.05 | 0.26 | 8.19 | 17.03 | 74.18 |
| 3H | 300 | 0.55 | 5.06 | 0.105 | 5.51 | 11.26 | 83.23 |
| 3I | 264 | 0.45 | 5.04 | 0 | 1.45 | 3.27 | 95.28 |
| 3J | 300 | 0.44 | 5.14 | 0 | 5.02 | 11.75 | 83.23 |

EXAMPLE 4

This example illustrates the uniqueness of complexed CuCl and CuCl$_2$ compared with powdered copper, FeCl$_3$, SnCl$_2$, NaCl and AgCl, in promoting the AlCl$_3$-catalyzed disproportionation of (CH$_3$)$_2$SiCl$_2$.

Examples 4A thru 4F (see Table 4 below) were performed in the 300 ml rocking autoclave according to the procedure of Example 2, except that additives other than CuCl were employed. The quantities of FeCl$_3$ and CuCl$_2$ were chosen so as to give molar ratios of 0.5 with AlCl$_3$. In example 4C with SnCl$_2$ as additive, the AlCl$_3$ concentration was 3 wt % and the SnCl$_2$/AlCl$_3$ molar ratio 0.47.

Examples 4G thru 4J (see Table 4 below) were performed in a 45 ml autoclave heated in a fluidized sand bath. The reagents [(CH$_3$)$_2$SiCl$_2$, AlCl$_3$ and additive] were charged to the autoclave in the nitrogen-filled glove bag as described in Example 2. The autoclave was then sealed and heated in the sand bath at 265° C. That temperature was maintained for 4 hours. Comparative experiments with AlCl$_3$ alone and AlCl$_3$ plus CuCl (molar ratio CuCl/AlCl$_3$=0.5) under these conditions are shown in Table 4 as Examples 4I and 4J.

The data showed that powdered copper, SnCl$_2$, FeCl$_3$, NaCl and AgCl did not promote the AlCl$_3$ catalysis of (CH$_3$)$_2$SiCl$_2$ disproportionation whereas complexed CuCl$_2$ and CuCl did.

TABLE 4

The effect of Cu, CuCl$_2$, SnCl$_2$, FeCl$_3$, NaCl, AgCl on the Disproportionation of (CH$_3$)$_2$SiCl$_2$ by AlCl$_3$ at 264° C. and 300° C.

| Example | Additive | Moles D | AlCl$_3$ Wt % | Additive Wt % | Temp. °C. | M Wt % | T Wt % | D Wt % |
|---|---|---|---|---|---|---|---|---|
| 4A | None | 0.45 | 5.04 | 0 | 264 | 1.45 | 3.27 | 95.28 |
| 4B | Powdered Cu | 0.55 | 5.04 | 2.13 | 264 | 1.73 | 3.35 | 94.92 |
| 4C | SnCl$_2$ | 0.47 | 3.0 | 2.0 | 300 | 3.30 | 6.87 | 89.83 |
| 4D | CuCl$_2$ | 0.52 | 5.01 | 2.59 | 300 | 6.78 | 17.54 | 75.67 |
| 4E | FeCl$_3$ | 0.46 | 5.01 | 3.24 | 300 | 5.00 | 13.14 | 81.86 |
| 4F | None | 0.44 | 5.14 | 0 | 300 | 5.51 | 11.26 | 83.23 |
| 4G | NaCl | 0.058 | 5.04 | 1.84 | 265 | 1.01 | 3.29 | 95.70 |
| 4H | AgCl | 0.058 | 5.04 | 2.67 | 265 | 1.05 | 3.30 | 95.65 |
| 4I | None | 0.058 | 5.04 | 0 | 265 | 1.09 | 3.43 | 95.48 |
| 4J | CuCl | 0.058 | 5.04 | 1.8 | 265 | 4.76 | 10.84 | 84.40 |

EXAMPLE 5

The four experiments (5A–5D) of this example were conducted separately in a 45 ml autoclave using the procedure described in Example 4G through 4J. Each experiment (5A–5D) was conducted with 7.5 gm (CH$_3$)$_2$SiCl$_2$ and the respective stated quantities of AlCl$_3$ and CuCl set forth in Table 5 below.

The data in Table 5 below demonstrates that the yield of (CH$_3$)$_3$SiCl from (CH$_3$)$_2$SiCl$_2$ disproportionation with CuCl—AlCl$_3$ catalyst mixture of 265° C. for 1, 2 and 4 hours was greater than the yield from the disproportionation catalyzed by AlCl$_3$ alone at 300° C. for 1 hour.

TABLE 5

(CH$_3$)$_2$SiCl$_2$ Disproportionation at Short Reaction Times and Low Catalyst Concentrations

| Example | Moles D | AlCl$_3$ Wt % | CuCl Wt % | Temp. °C. | Time Hr | M Wt % | T Wt % | D Wt % |
|---|---|---|---|---|---|---|---|---|
| 5A | 0.058 | 4.93 | 1.75 | 265 | 1 | 0.62 | 3.18 | 96.20 |
| 5B | 0.058 | 5.08 | 1.80 | 265 | 2 | 2.07 | 3.83 | 94.22 |
| 5C | 0.058 | 0.50 | 0.19 | 265 | 4 | 0.53 | 3.40 | 95.51 |
| 5D | 0.058 | 5.08 | 0 | 300 | 1 | — | — | 100.00 |

EXAMPLE 6

This example demonstrates the reusability of the catalyst complex of this invention.

For Example 6A, 55.6 gm (CH$_3$)$_2$SiCl$_2$ was reacted in the presence of a complex formed from a mixture of 3.2 gm AlCl$_3$ and 1.2 gm CuCl in a 300 ml autoclave at 310° C. using the procedure of Example 2. The molar ratio of CuCl to AlCl$_3$ was 0.5. After 5.2 hours at 310° C. the autoclave was cooled to 100° C., which is below the melting point of the CuCl—AlCl$_3$ catalyst but above the normal boiling points of the methylchlorosilanes in the reaction product. The valved outlet of the autoclave was connected to an evacuated cooled (with dry-ice and isopropanol) 150 ml stainless steel sample cylinder.

On opening the valves of the autoclave and the cylinder, the methylchlorosilane mixture distilled from the autoclave into the sample cylinder and the catalyst complex remained in the autoclave. 38.7 gm of liquid was so transferred. Thereafter the autoclave and sample cylinder were disconnected and the sample cylinder warmed to room temperature. Any residual vacuum was released under nitrogen prior to analysis of the reaction product.

For Example 6B fresh $(CH_3)_2SiCl_2$ (44.0 gm) was placed in another 150 ml stainless steel sample cylinder with a valve attached at each end. One end of the cylinder was connected to the valved inlet of the autoclave (containing the catalyst complex from example 6A above) and the other end to a nitrogen source pressurized to 30 psig. The dimethyldichlorosilane was transferred to the autoclave by first opening the cylinder valve distal from the autoclave (i.e., to pressurize the cylinder which contained the dimethyldichlorosilane), followed by opening the valve proximal to the autoclave and finally opening the autoclave valve itself. After the transfer the valves were closed and the autoclave disconnected from the sample cylinder. The autoclave was reheated to 310° C. and maintained at that temperature for 4.1 hours. 51.9 gm of liquid product was recovered by vacuum transfer from the cooled (100° C.) autoclave as described above. Product analysis of the two disproportionation experiments is shown in Table 6.

The data in Table 6 below demonstrates that the catalyst complex used in the process of this invention is reusable. $(CH_3)_3SiCl$ and $CH_3SiCl_3$ were also produced in Example 6B in good yields; the catalyst in Example 6A was the same catalyst used in Example 6B, and no additional CuCl or $AlCl_3$ was added to Example 6B.

TABLE 6

Reuse of CuCl—$AlCl_3$ Catalyst Complex in the Disproportionation of $(CH_3)_2SiCl_2$ at 310° C.

| Example | HCl Wt % | MD Wt % | M Wt % | T Wt % | D Wt % |
|---|---|---|---|---|---|
| 6A | 0.26 | 0.44 | 7.48 | 15.20 | 76.62 |
| 6B | 1.17 | 2.15 | 8.47 | 15.07 | 73.15 |

EXAMPLE 7

This example illustrates the redistribution of $(CH_3)_3SiCl$ and $CH_3SiCl_3$ by CuCl—$AlCl_3$ catalyst complex.

$CH_3SiCl_3$ (2.9 gm, 0.0194 mole) and $(CH_3)_3SiCl$ (2.15 gm, 0.0198 mole) were charged to a 45 ml autoclave along with a mixture of 0.376 gm $AlCl_3$ and 0.14 gm CuCl using the procedure in Example 4G and 4J. The sealed autoclave was then heated to 265° C. in a fluidized sand bath and maintained there for 4 hours. Thereafter the autoclave was cooled to room temperature and its contents subsequently analyzed by gc. The analytical data (see Table 7) show that the desired product of the redistribution, i.e. $(CH_3)_2SiCl_2$, accounted for over 50 wt % of the reaction end product.

TABLE 7

Redistribution of $(CH_3)_3SiCl$ and $CH_3SiCl_3$ by CuCl—$AlCl_3$ (molar ratio 0.5) at 265° C., 370 psig

| Example | M Wt % | T Wt% | D Wt % |
|---|---|---|---|
| 7A | 20.68 | 26.09 | 53.63 |

EXAMPLE 8

This example illustrates that the CuCl—$AlCl_3$ complexes catalyze the redistribution of methylchlorosilanes even at 23° C.

The catalyst was prepared by heating 1.11 gm $AlCl_3$ and 0.43 gm CuCl in an evacuated glass ampoule 300° C. as described in Example 1A. The solid was retrieved by breaking the ampoule in a $N_2$-filled glove bag. The 1.54 gm catalyst complex having a CuCl/$AlCl_3$ molar ratio of 0.5 was added to 22 gm of a methylchlorosilane mixture containing 43.98% $(CH_3)_4Si$, 8.91% $(CH_3)_2SiHCl$ and 46.97% $(CH_3)_2SiCl_2$ in a 250 ml 3-neck round bottom flask. A reflux condenser was affixed to one neck, a thermometer to another and a serum cap to the third. The serum cap facilitated periodic sampling of the magnetically stirred reaction mixture for gc analysis. Temperature was maintained at 23° C.

The results (see Table 8 below) demonstrate that $(CH_3)_3SiCl$ was formed from the redistribution.

TABLE 8

Redistribution of $(CH_3)_4Si$("Q") $(CH_3)_2SiHCl$ ("DM") and $(CH_3)_2SiCl_2$ ("D") by CuCl—$AlCl_3$ (molar ratio = 0.5) at 23° C.

| Time, Hr | Q wt % | DM wt % | M wt % | D wt % |
|---|---|---|---|---|
| 0 | 43.98 | 8.91 | 0.14 | 46.97 |
| 0.5 | 42.81 | 8.66 | 2.22 | 46.31 |
| 1.0 | 42.91 | 8.48 | 2.92 | 45.70 |
| 1.5 | 43.98 | 8.81 | 3.28 | 43.93 |
| 2.0 | 41.65 | 8.39 | 3.33 | 47.81 |
| 3.0 | 41.52 | 8.61 | 3.46 | 46.40 |

What is claimed is:

1. A process for effecting the redistribution of at least one organic group bonded to a silicon atom by a silicon to carbon bond and at least one halogen atom bonded to a silicon atom which process comprises:
   (1) forming a reaction mixture of
      (a) a first silane or first mixture of silanes containing at least one organic group bonded to a silicon atom by a silicon to carbon bond and at least one halogen atom bonded to a silicon atom;
      (b) a catalytic amount of a complex of $AlX_3$ and $CuX_n$ wherein n is 1 or 2 and X is a halogen atom; and
   (2) maintaining such mixture at a temperature and pressure at which said group and atom in (1)(a) redistribute to form a second silane or a second mixture of silanes different from said silane or said first mixture of silanes.

2. A process as recited in claim 1 wherein the complex of $AlX_3$ and $CuX_n$ is formed from a mixture of $AlX_3$ and $CuX_n$ wherein the molar ratio of $CuX_n$ to $AlX_3$ is at least about 0.05:1.

3. A process as recited in claim 2 wherein the complex of $AlX_3$ and $CuX_n$ is formed from a mixture of $AlX_3$ and $CuX_n$ wherein the molar ratio of $CuX_n$ to $AlX_3$ is about 0.25:1 to about 0.6:1.

4. A process as recited in claim 3 wherein the complex of $AlX_3$ and $CuX_n$ is formed from a mixture of $AlX_3$ and $CuX_n$ wherein the molar ratio of $CuX_n$ to $AlX_3$ is about 0.5:1.

5. A process for the catalytic disproportionation of a diorganodihalosilane of the formula $$R_2SiX_2$$

wherein R is alkyl or aryl and X is halogen which comprises contacting the diorganodihalosilane with a catalytic amount of a complex of $AlX_3$ and $CuX_n$, wherein n is 1 or 2 and X is as defined above, at a temperature greater than 200° C. and under superatmospheric pressure.

6. A process as recited in claim 5 wherein R is $C_1$–$C_4$ alkyl.

7. A process as recited in claim 5 wherein R is methyl and X is Cl.

8. A process as recited in claim 5 wherein the process is conducted at a temperature in the range of about 250° C. to about 350° C.

9. A process as recited in claim 8 wherein the process is conducted at a temperature in the range of about 250° C. to about 300° C.

10. A process as recited in claim 8 wherein the process is conducted at a pressure in the range of about 400 to about 700 psi.

11. A process as recited in claim 10 wherein the process is conducted at a pressure in the range of about 450 to about 550 psi.

12. A process as recited in claim 11 wherein the process is conducted under autogenous conditions.

13. A process as recited in claim 5 wherein the complex of $AlX_3$ and $CuX_n$ is formed from a mixture of $AlX_3$ and $CuX_n$ wherein the molar ratio of $CuX_n$ to $AlX_3$ is at least about 0.05:1.

14. A process as recited in claim 13 wherein the complex of $AlX_3$ and $CuX_n$ is formed from a mixture of $AlX_3$ and $CuX_n$ wherein the molar ratio of $CuX_n$ to $AlX_3$ is about 0.25:1 to about 0.6:1.

15. A process as recited in claim 14 wherein the complex of $AlX_3$ and $CuX_n$ is formed from a mixture of $AlX_3$ and $CuX_n$ wherein the molar ratio of $CuX_n$ to $AlX_3$ is about 0.5:1.

16. A process for the disproportionation of dimethyldichlorosilane which comprises contacting the dimethyldichlorosilane with a catalytic amount of a complex of $CuCl_n$ and $AlCl_3$, wherein n is 1 or 2, at a temperature greater than 200° C. and under superatmospheric pressure.

17. A process as recited in claim 16 wherein the process is conducted at a temperature in the range of abut 250° C. to about 300° C.

18. A process as recited in claim 16 wherein the process is conducted at a pressure of about 450 to about 550 psi.

19. A process as recited in claim 18 wherein the process is conducted under autogenous conditions.

20. A process as recited in claim 16 wherein the complex of $AlCl_3$ and $CuCl_n$ is formed from a mixture of $AlCl_3$ and $CuCl_n$ wherein the molar ratio of $CuCl_n$ to $AlCl_3$ is about 0.25:1 to about 0.6:1.

21. A process as recited in claim 20 wherein the complex of $AlCl_3$ and $CuCl_n$ is formed from a mixture of $AlCl_3$ and $CuCl_n$ wherein the molar ratio of $CuCl_n$ to $AlCl_3$ is about 0.5:1.

22. A process as recited in claim 16 wherein the complex of $AlCl_3$ and $CuCl_n$ is present in the disproportionation reation mixture at a concentration of about 5% to about 10%.

23. A process for the catalytic redistribution of a mixture of organohalosilanes having the formulas:

$$R_mSiX_{4-m} \text{ and } R_pSiHX_{3-p}$$

wherein R and X are as defined in claim 1, m is 1 to 4 inclusive and p is 1 to 3 inclusive, which comprises contacting the mixture of organohalosilanes with a catalytic amount of a complex of $AlX_3$ and $CuX_n$, wherein n is 1 or 2.

24. A process as recited in claim 23 wherein R is $C_1$–$C_4$ and X is Cl.

25. A process as recited in claim 23 wherein the complex of $AlX_3$ and $CuX_n$ is formed from a mixture of $AlX_3$ and $CuX_n$ wherein the molar ratio of $CuX_n$ to $AlX_3$ is at least about 0.05:1.

26. A process as recited in claim 25 wherein the complex of $AlX_3$ and $CuX_n$ is formed from a mixture of $AlX_3$ and $CuX_n$ wherein the molar ratio of $CuX_n$ to $AlX_3$ in about 0.25:1 to about 0.6:1.

* * * * *